United States Patent [19]

Lustig et al.

[11] 4,285,671

[45] Aug. 25, 1981

[54] CONTRA ANGLE WITH INTERCHANGEABLE GEARED TOOLS AND THE LIKE

[76] Inventors: Leopold P. Lustig, 304 Greenwood St., Newton Center, Mass. 02159; Sigrid Bechter, Strassberger Strasse 65, 8000 Munchen 40, Fed. Rep. of Germany

[21] Appl. No.: 970,468

[22] Filed: Dec. 18, 1978

[51] Int. Cl.³ .................................................. A61C 1/08
[52] U.S. Cl. ...................................... 433/126; 74/462; 433/133
[58] Field of Search ......... 74/462, 460, 457, DIG. 10, 74/333, 339; 192/20; 310/83; 433/105, 126, 133

[56] References Cited

U.S. PATENT DOCUMENTS

| | | | |
|---|---|---|---|
| 1,329,535 | 2/1920 | McGrath | 74/462 |
| 2,028,786 | 1/1936 | Lamatsch | 74/462 |
| 2,923,389 | 2/1960 | Perkins | 74/339 |
| 3,175,110 | 3/1965 | Kohlhagen | 310/83 |
| 3,265,173 | 8/1966 | Russell | 192/108 |
| 4,053,983 | 10/1977 | Flatland | 433/133 |
| 4,110,054 | 8/1978 | Moeller, Jr. | 74/DIG. 10 |

FOREIGN PATENT DOCUMENTS 909413  5/1946  France ........................................ 74/462

*Primary Examiner*—Gene Mancene
*Attorney, Agent, or Firm*—Alfred H. Rosen

[57] ABSTRACT

A contra-angle housing made in two parts hinged together at one end encloses a drive shaft with drive gears at one end, and a geared hub for a dental tool or the like supported in apertures in or through the housing parts transverse to the drive shaft. A latch mechanism can be manually operated to release the two housing parts so that they can be opened to change tools, clutches or the like with integral gear hubs. When the housing parts are closed the gears on the hub automatically mesh with the drive shaft gears. Reinforced gears which can be made of molded plastic make possible low-cost interchangeable tools with integral gears.

8 Claims, 12 Drawing Figures

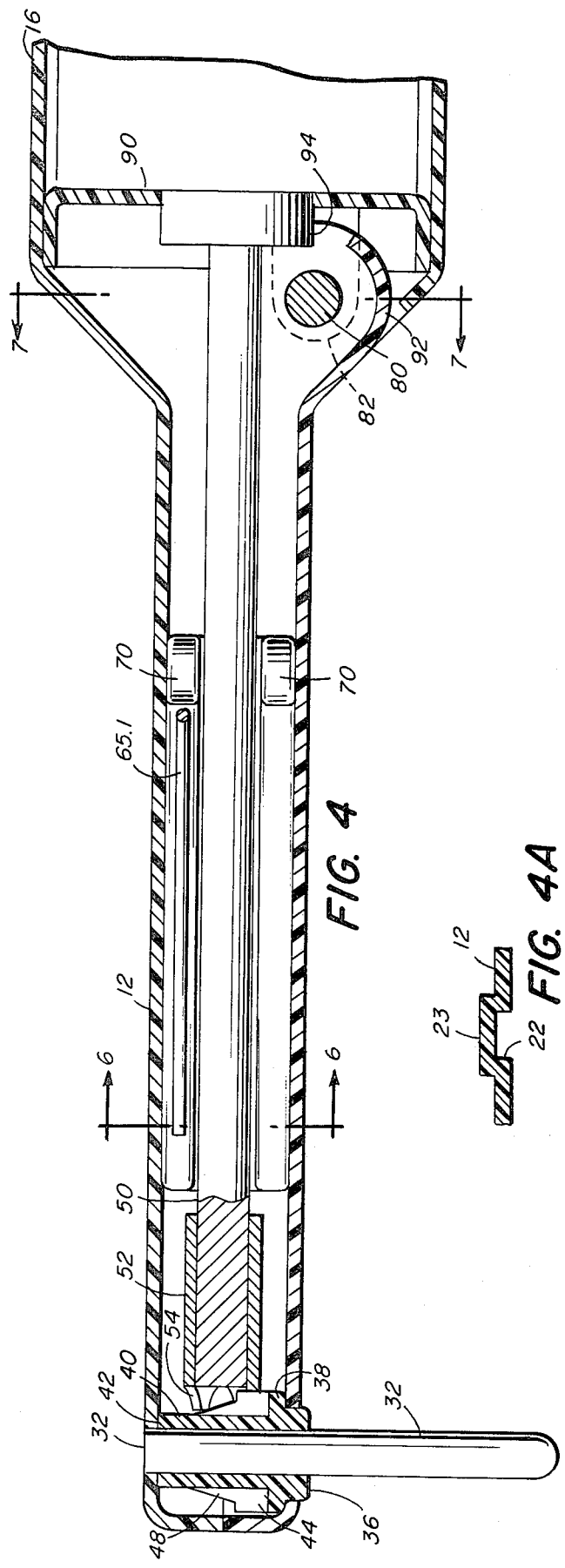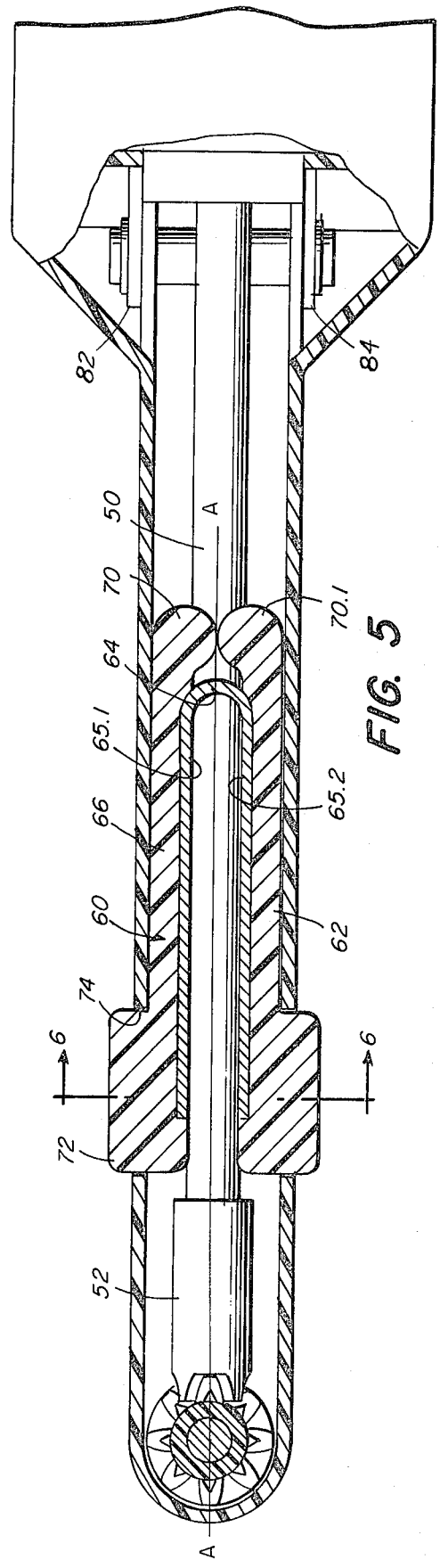

CONTRA ANGLE WITH INTERCHANGEABLE GEARED TOOLS AND THE LIKE

BACKGROUND OF THE INVENTION

Dental hand-pieces of the type known as "contra-angle" tool holders generally include an elongated tubular housing arranged to be coupled at one end to the housing of a dental motor and enclosing an alley for a drive shaft which couples to the motor. At the other end the drive shaft is coupled to a tool shaft, or a tool clutch, through gears that rotate the tool on an axis transverse to the drive shaft axis, and a stub housing is provided to enclose the tool and the direction-changing gears. Typically of contra-angle tool holders, the stub-housing is provided with openings at both ends, one to receive the tool and the other to give access to mechanism to lock the tool in place. U.S. Pat. No. 3,369,298 shows one example of such contra-angle tool holders; in that example a clutch is permanently rotatably fixed in the stub housing, and a tool can be removably inserted into the clutch from one end, while a lock mechanism is provided at the other end. In other examples of such contra-angles, the tool is inserted through the housing from the lock-end of the stub housing, and a removable (e.g. threaded) cap is provided at the same end to perform the lock function. As contra angles are made smaller, these parts, especially removable caps, become so small that they are difficult to manipulate and are easily lost, wasting the time of the dentist. The housing structure required to provide a shaft alley for the drive shaft, communicating at an end with a transverse passage across the shaft alley for the tool or the clutch, are expensive to make, particularly in the smaller sizes. The choices of manufacturing process that can be used to make them are limited to processes that are suitable for making rigid tubular parts out of materials that are suitable for dental use, to precision standards.

GENERAL NATURE OF THE INVENTION

This invention provides a contra-angle housing made of two shell-like mating parts which are hinged together at one end and give access at their other ends to the interior of the housing for installing and removing tools, clutches and the like simply by opening the two parts like the beak of a bird. Bringing the two parts together and latching them one to the other forms a housing enclosing a drive shaft and angle-changing gears. The housing parts can be made by a wide range of processes, including molding and stamping, since they are open throughout their full lengths. The drive shaft is preferably fixed with relation to one of the shell parts, and the placement of bearings and latch mechanisms in them as well as the installation and exchange of tools and clutches, are easily done. In a preferred embodiment, a pair of holes, one in each shell part, or a hole in one part and a recess in the other, located so that when the shell parts are brought together and closed they define a passage across the end of the drive shaft alley, suffice to locate and support a tool or a clutch in the housing. A special design of tool or clutch is also provided with unique gears for use in the invention, such that a drive gear at the end of the drive shaft will automatically mesh with the tool gears when the shell parts are closed after placing a new tool or clutch in the housing. The tool gear design provides reinforcement for the gear teeth such that the tool gears can be formed in a plastics material as well as a metal, including the possibility of precision molding or casting a gear assembly, so that disposable tools will be more economically manufactured. For example, a replaceable tool or a mandrel can be made of a plastics material in which the shaft is fixed.

It is known from U.S. Pat. No. 4,053,983 to make a contra-angle housing out of two housing shells which have faces meeting on a common plane, but in that patent the two shells are fixedly held together in a threaded casing, and a geared hub in the housing is mounted for rotation on a tungsten carbide pin which is fixed in one of the shells. The hub is internally threaded to receive a dental tool from outside the housing. There is no provision for opening the two shells during use of the contra-angle, or for changing the tool gear component.

The invention is illustrated in the accompanying drawings of an embodiment that is presently preferred, and is described below with reference to the drawings.

BRIEF DESCRIPTION OF THE DRAWINGS

FIG. 4 is an enlarged side-sectional view through closed shell-housing;

FIG. 4A shows an alternative part in FIG. 4;

FIG. 5 is a sectional view on line 5–5 of FIGS. 4 and 6;

DETAILED DESCRIPTION OF THE DRAWINGS

Figure 1:
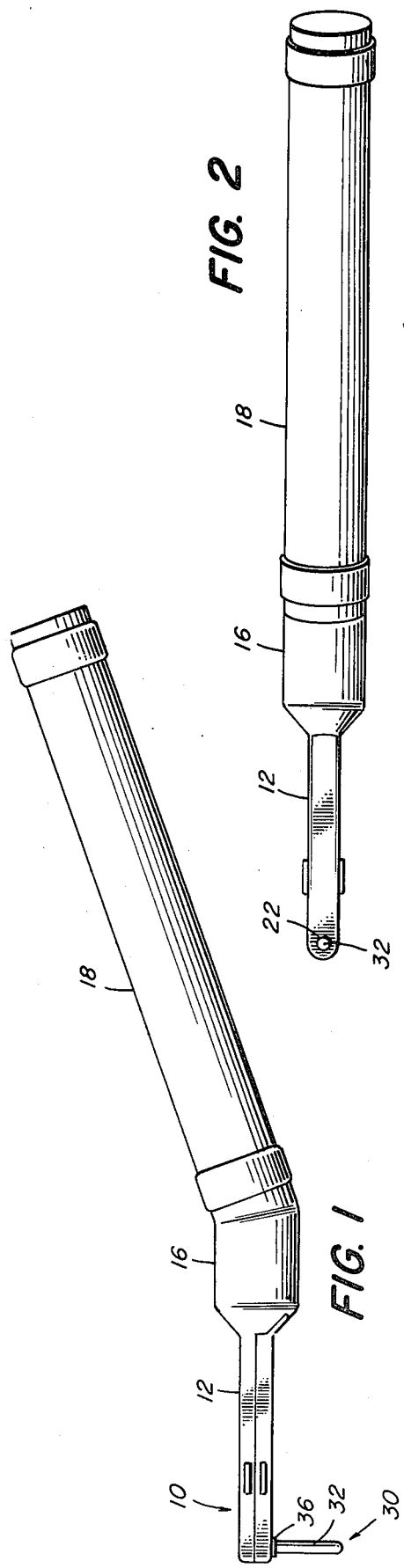
FIG. 1 is a side view of a contra-angle fitted to a handle.
Figure 2:
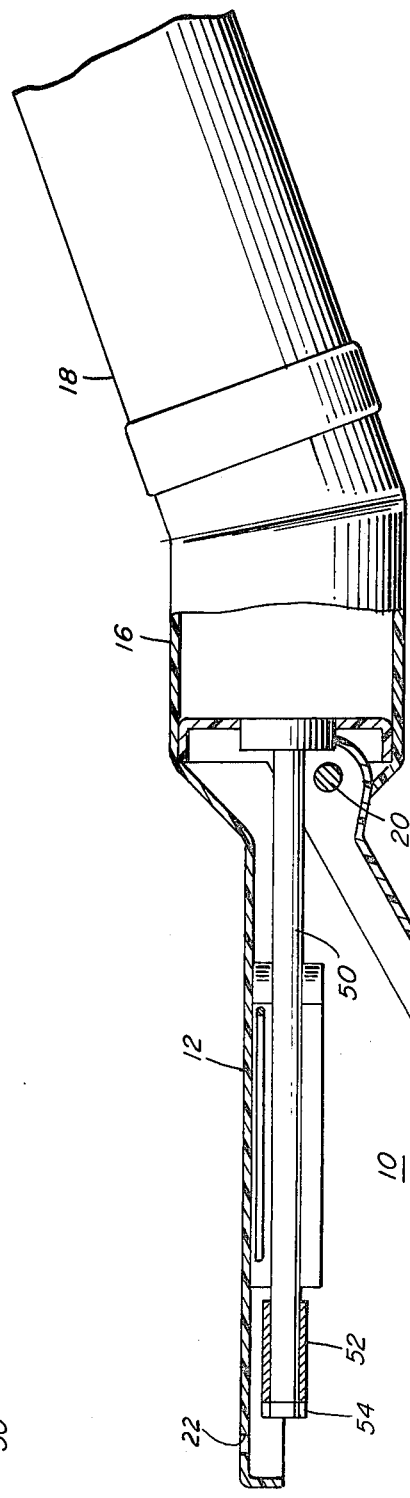
FIG. 2 is a top view of FIG. 1.
Figure 3:
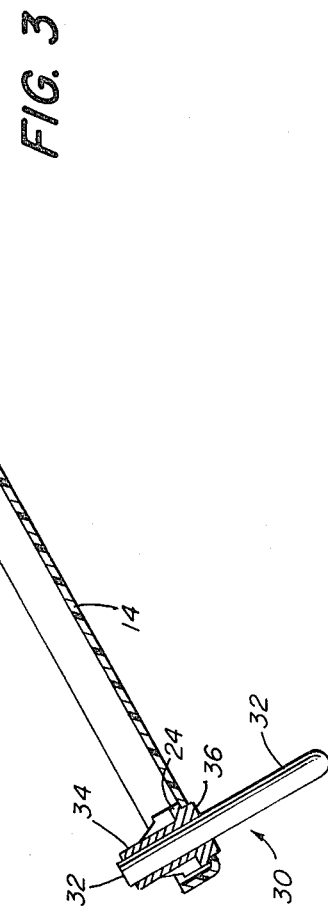
FIG. 3 is an enlarged partial view showing the housing of the contra-angle open to give access to the interior and to a changeable tool in the housing.

The invention is generally illustrated in FIGS. 1, 2 and 3. A contra-angle, generally designated by reference 10, has a housing made in two shell-like parts 12 and 14 which are attached to a support 16 which in turn is attached to a handle 18. The first shell part 12 is fixed to the support and the second shell part 14 is attached to the support with a hinge 20 so that it can be swung away from the fixed shell like the beak of a bird, as is shown in FIG. 3. The support 16 can be attached to the handle 18 in any way that is convenient, for example, disconnectibly as is well-known. The invention is not concerned with that detail, and so it is not illustrated.

Figure 8:
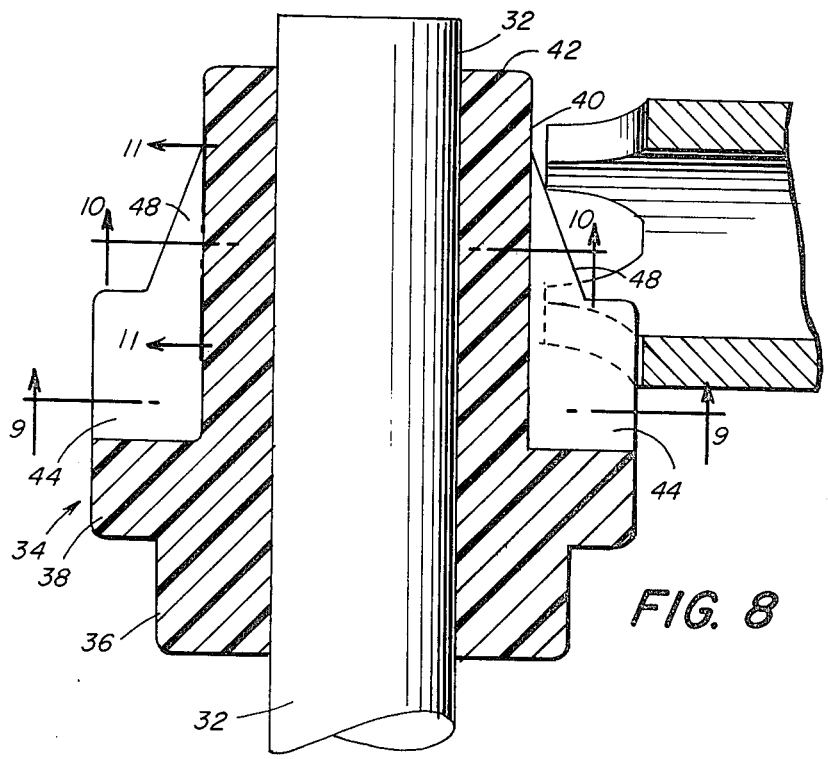
FIG. 8 is a greatly-enlarged section through the gear and shaft portion of the tool shown in FIGS. 1–7.
Figure 9:
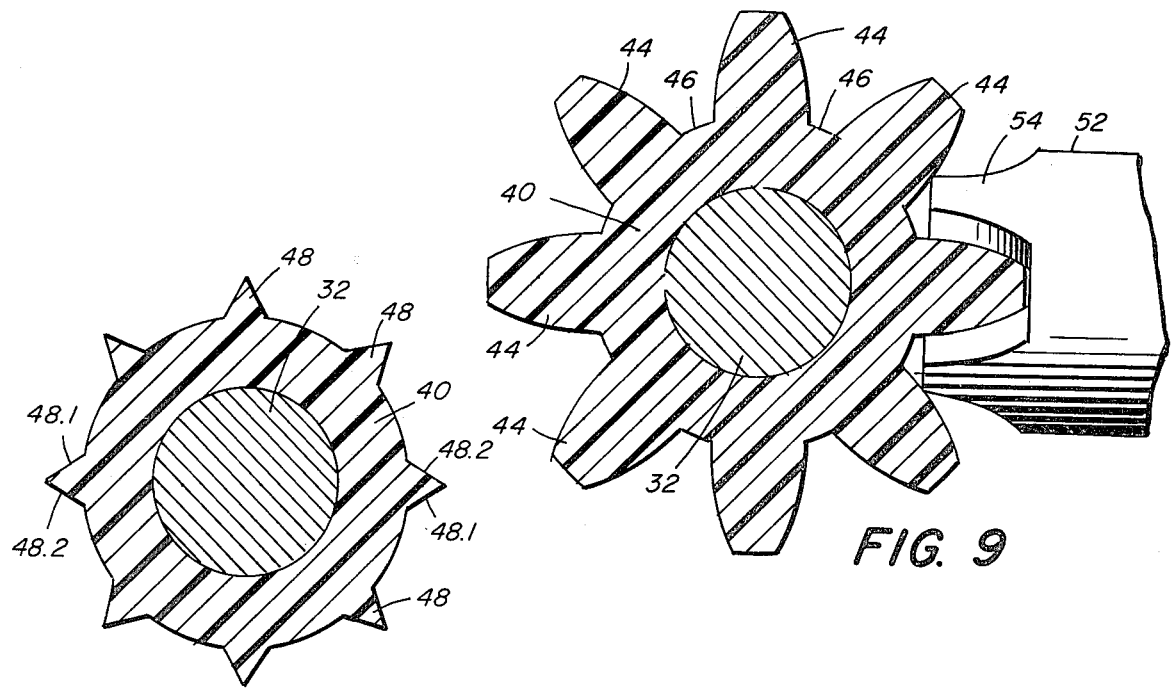
FIG. 9 is a section on line 9—9 of FIG. 8.

A dental tool 30 is schematically illustrated, to represent any tool it may be desired to use. According to the invention, the tool comprises a shaft 32 to which a gear and bearing sleeve 34 is fixed. FIGS. 8 and 9 illustrate these components in detail. The sleeve 34 has a lower bearing portion 36 and 38 and an upper bearing portion 42. Between the upper bearing portion 42 and the nearer lower bearing portion 38 the sleeve has an array of spur gear teeth 44 projecting radially away from the inner sleeve part 40. The gear teeth are fixed at one end to the lower bearing portion 38, and at the other (upper) end the gear teeth have extensions 48 which taper toward the inner sleeve part 40. In this way, each gear tooth is physically supported at each end by a part of the gear and bearing sleeve 34. As illustrated in FIG. 9, the gear teeth 44 are separated from each other at their roots, and an exposed surface 46 of the inner sleeve part 40 intervenes between each tooth and its neighbors.

Returning to FIG. 3, it will be seen that the hinged shell part 14 has a hole 24 into which the outermost lower bearing portion 36 of the tool 30 fits, and when the tool is fitted into the hole 24 the inner lower bearing portion 38 rests on the inner surface of the hinged shell part. When the shell parts are closed together, as is shown in FIGS. 1 and 2, the upper bearing portion 42 of the sleeve 34 will come into contact with an inner surface of the fixed shell part 12, which has a hole 22 through it located opposite the hole 24 in the hinged shell part 14. The shaft 32 extends beyond the upper bearing portion 42 into the hole 22, when the two shell parts are closed, as can be seen in FIG. 2. While the invention includes the possibility that the tool 30 can be supported in anti-friction bearings, the simpler illustration which has been described is sufficient to disclose the invention.

Figure 10:
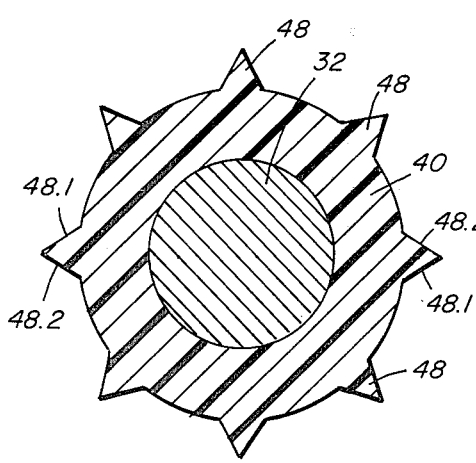
FIG. 10 is a section on line 10—10 of FIG. 8.
Figure 11:
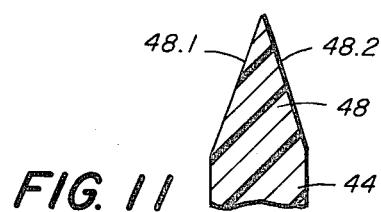
FIG. 11 is a view of a gear tooth partial section on line 11—11 of FIG. 8.

Further details are illustrated in the enlarged view of FIGS. 4-7, inclusive. A main drive shaft 50 is rotatably fixed in the support 16, to which the first shell part 12 is fixed. A crown gear hub 52 with crown gear teeth 54 is fitted to the free end of the drive shaft, in position to engage the spur gear teeth 44 when the two shell parts 12, 14 are closed, as shown in FIGS. 1 and 4. When the two shell parts are open as shown in FIG. 3, the drive shaft 50 remains with the first shell part 12 and the spur gear teeth 44 are separated from the crown gear teeth 54. When the two shell parts 12, 14 are brought to a closed position from the open position with a tool 30 in place, as shown in FIG. 3, the tapered extensions 48 of the spur gear teeth 44 come first into contact with the crown gear teeth 54. Referring to FIGS. 10 and 11, the tapered extensions 48 are tapered at the root as well as in height, providing sloped sides 48.1 and 48.2 on one of which each crown gear tooth first makes contact. The spur gear and bearing sleeve can rotate with the tool shaft 32, and when the crown gear teeth 54 meet a sloping side 48.1 or 48.2 of one or more tapered extensions 48, the spur gears 44 are thereby automatically aligned into mesh with the crown gear teeth as the shell parts 12, 14 are closed one on the other.

Figure 6:
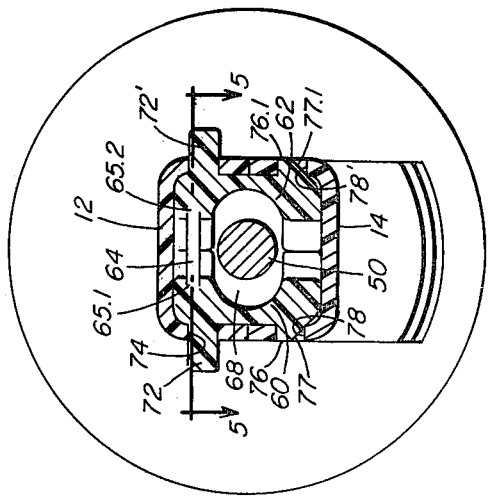
FIG. 6 is a cross-section on line 6–6 of FIGS. 4 and 5.

Referring in particular to FIGS. 4, 5 and 6, the two shell parts 12, 14 are held together releasably by a latch mechanism consisting of two latch parts 60 and 62 and a U-shaped spring 64. The latch parts can be made of a plastics material, as illustrated by the section-hatching in FIG. 5; alternatively they can be made of a metal.

Each latch part is the mirror image of the other. The first latch part 60 is described in detail. A main body 66 extends a distance along the axis A-A (FIG. 5) within the shell parts 12, 14 and fills the space between them transverse to the long axis when the shell parts are closed, with the exception of a longitudinal void 68 (FIG. 6) providing an alley for the drive shaft 50. At the end nearer to the support 16 a rounded bearing portion 70 extends over and under the shaft 50 to the longitudinal center, where it makes rolling contact with the corresponding bearing portion 70.1 of the second latch part 62. The latch parts 60, 62 are otherwise separated from each other throughout their lengths. A press-bar 72 extends through a slot 74 in a side wall of first shell part 12. A latch bar 76 with a sloped side 77 fits through a slot 78 in the second shell part 14 when the two shell parts are closed. The spring 64 has long arms 65.1 and 65.2 (FIG. 5) which fit into corresponding elongated grooves in the inner walls of the first and second latch parts, respectively, substantially in the same plane as the press bars 72 and 72'.

By pressing on the press bars 72 and 72' the latch bars 76.1 and 76' (FIG. 6) are withdrawn inwardly from their respective slots 78 and 78' in the second shell part 14, and the shell parts can be opened. The latch parts 60, 62 are retained in the first shell part by the press bars 72 and 72' and the spring 64. When the shell parts are moved to the closed position the second shell part first meets the sloped sides 77 and 77' of the latch bars 76 and 76', and pushes the latch parts together, compressing the arms 65.1 and 65.2 of the spring 64, so that the latch bars fit within the second shell part. When the two shell parts meet the latch bars move into the slots 78 and 78', respectively, of the second shell part under expanding force from the spring 64, latching the two shell parts together.

Figure 7:
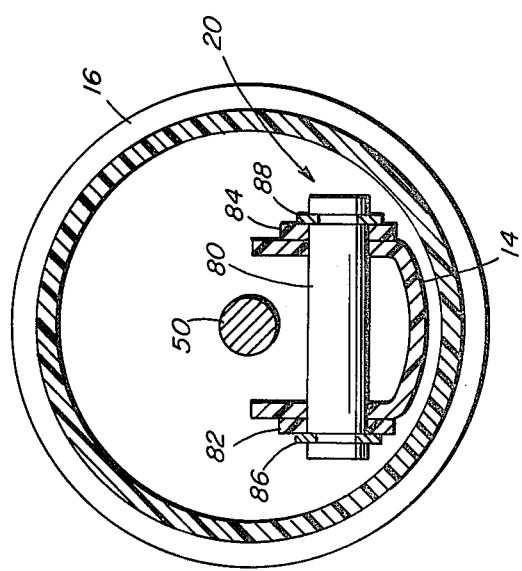
FIG. 7 is a cross-section on line 7—7 of FIG. 4.

The hinge 20 is further illustrated in FIGS. 5 and 7. It includes a hinge pin 80 around which the second shell part 14 can rotate, bearing plates 82, 84, and retainer 86, 88 of the snap-ring type to keep the hinge pin fixed in its place. The bearing plates 82, 84 are extensions on a closure plate 90 fitted within the support 16. The second shell part 14 has a cover 92 extending around the hinge pin 80 and toward a stop arm 94 (FIG. 4) fixed on the closure plate, for limiting the arc through which the second shell part 14 can move when it is opened.

As shown in FIG. 4A, the hole 22 in the first shell part can be fitted with a cover 23, if desired, for sanitary purposes. It will be understood also that an anti-friction bearing assembly can be fitted into the space within the cover 23.

The shell parts can be made of a plastics material as illustrated. Alternatively, they can be made of metal, as is the drive shaft 50, in order to provide the possibility to make the contrangle small in size with adequate strength. Accordingly, the shell parts can be stamped, drawn or otherwise formed from sheet stock, or cast, molded or sintered, as desired.

We claim:

1. A spur gear on a shaft for rotating the shaft around its longitudinal axis, in which gear teeth project radially away from the shaft axis and extend a distance in the axial direction, characterized in that at one end of the gear the teeth taper radially toward the shaft and simultaneously the root thickness of each tooth tapers uniformly on both sides circumferentially toward a point, whereby the teeth at said one end are tapered subtantially conically to a point.

2. A spur gear according to claim 1, in combination with a drive gear arranged for rotation about a second axis which is angularly related to said shaft axis, and means to move the drive gear in the plane common to both axes for side-wise approaching the spur gear at the tapered end to engage the two gears.

3. A dental tool having a shaft and a gear according to claim 1 on the shaft, characterized in that the gear is formed in a unitary tubular plastics body having at the end opposite the tapered ends of the teeth a flange for supporting the gear teeth followed by a hub for locating the gear in a support, and at the other end adjacent the tapered ends of the gear teeth a bearing surface across the tubular body.

4. A tool according to claim 3 in combination with a dental instrument characterized by an elongated hollow enclosure made of two complementary half-shell parts connected together at one end by a hinge and having at the other end a pair of registered openings for supporting the tool at two separated locations, locking means to hold the two parts together with the tool shaft in the openings and the spur gear between the openings surrounded by the enclosure, the half shells being releasable by said locking means so that they can be opened around the hinge like a beak, providing space to remove one tool and substitute another, wherein the hub is located in one of the registered openings and the bearing surface is located adjacent the other registered opening when the two half-shell parts are closed.

5. A rotatable tool element including a shaft and a spur gear on the shaft for rotating the shaft around its longitudinal axis, characterized by a tubular body fitted to the shaft, the body having spur gear teeth which project radially away from the shaft axis and extend along the body a distance in the axial direction, each tooth having at one end a substantially pointed part which tapers radially toward the shaft axis relative to displacement along the body in the axial direction, said part also tapering circumferentially toward a point relative to said displacement, each tooth being fixed at the other end to an annular part extending radially from the body, for providing additional support to the gear teeth.

6. A tool element according to claim 5 in which the shaft is made of a metal, and the tubular body is made of a plastics material.

7. A tool element according to claim 5 in which the shaft is made of a metal, and the tubular body with gear teeth and supports are a unitary component made of a plastics material.

8. A tool according to claim 5 in combination with a dental instrument characterized by an elongated hollow enclosure made of two complementary half-shell parts connected together at one end by a hinge and having at the other end a pair of registered openings for supporting the tool at two separated locations, locking means to hold the two parts together with the tool shaft in the openings and the spur gear between the openings surrounded by the enclosure, the half-shells being releasable by said locking means so that they can be opened around the hinge like a beak, providing space to remove one tool and substitute another, said instrument having tool-drive means including a drive shaft rotatable around an axis that is fixed in direction relative to a first of the half-shell parts and a tool-drive gear on the end of the shaft so that when the two half-shell parts are opened the tool-drive gear is moved relative to the second half-shell part, and when said tool having a spur gear according to claim 3 is placed on the second half-shell part with its shaft passing through the registered opening therein and the tapered end of the spur gear looking toward the first half-shell part and the tool-drive gear, then when the two half-shell parts are moved from the open position to the closed position the tool-drive gear approaches the spur gear at the tapered end, to assure that the two gears will engage.

* * * * *